United States Patent [19]

Silverstein

[11] Patent Number: 5,702,344
[45] Date of Patent: Dec. 30, 1997

[54] SAFE ENDOSCOPIC ACCESSORY

[75] Inventor: Fred E. Silverstein, Seattle, Wash.

[73] Assignee: University of Washington, Seattle, Wash.

[21] Appl. No.: 454,543

[22] Filed: May 30, 1995

[51] Int. Cl.⁶ ............................................. A61B 1/00
[52] U.S. Cl. ........................ 600/104; 600/106; 600/123; 600/153; 604/164
[58] Field of Search ........................ 600/104, 106, 600/123, 153–154; 604/158, 162, 164–165, 167, 169, 171; 606/181, 185

[56] References Cited

U.S. PATENT DOCUMENTS

| | | | |
|---|---|---|---|
| 2,621,651 | 12/1952 | Wallace | 600/104 |
| 3,421,509 | 1/1969 | Fiore | 604/171 |
| 4,222,380 | 9/1980 | Terayama | 600/104 X |
| 4,240,411 | 12/1980 | Hosono | 604/167 X |
| 4,254,762 | 3/1981 | Yoon | 128/4 |
| 4,321,915 | 3/1982 | Leighton et al. | 128/4 |
| 4,327,735 | 5/1982 | Hampson | 128/348 |
| 4,329,995 | 5/1982 | Anthracite | 128/350 R |
| 4,356,610 | 11/1982 | Hon et al. | 29/157 R |
| 4,524,770 | 6/1985 | Orandi | 128/303.1 |
| 4,535,773 | 8/1985 | Yoon | 604/51 |
| 4,646,722 | 3/1987 | Silverstein et al. | 128/4 |
| 4,664,259 | 5/1987 | Landis | 604/162 X |
| 4,668,226 | 5/1987 | Omata et al. | 604/272 |
| 4,763,662 | 8/1988 | Yokoi | 128/660 |
| 4,763,667 | 8/1988 | Manzo | 128/750 |
| 4,808,168 | 2/1989 | Waring | 604/158 |
| 4,854,302 | 8/1989 | Allred, III | 128/6 |
| 4,907,598 | 3/1990 | Bauer | 128/753 |
| 4,940,458 | 7/1990 | Cohn | 604/51 |
| 4,944,728 | 7/1990 | Carrell et al. | 604/164 |
| 5,019,042 | 5/1991 | Sahota | 604/101 |
| 5,037,433 | 8/1991 | Wilk et al. | 606/139 |
| 5,061,244 | 10/1991 | Yurkewych et al. | 604/164 |
| 5,078,681 | 1/1992 | Kawashima | 604/53 |
| 5,135,504 | 8/1992 | McLees | 604/164 |
| 5,193,525 | 3/1993 | Silverstein et al. | 600/123 X |
| 5,226,426 | 7/1993 | Yoon | 128/753 |
| 5,419,766 | 5/1995 | Chang et al. | 604/110 |

FOREIGN PATENT DOCUMENTS

| | | | |
|---|---|---|---|
| 141 108 | 4/1980 | Germany | A61B 10/00 |
| 1 405 025 | 9/1975 | United Kingdom . | |

*Primary Examiner*—Beverly M. Flanagan
*Attorney, Agent, or Firm*—Seed and Berry LLP

[57] ABSTRACT

An endoscopic accessory comprising a catheter with axial walls defining an interior area, an elongated tool shaft slidably positioned within the interior area of the catheter, an endoscopic tool attached to the distal end of the tool shaft, and a retaining member connected to the catheter to prevent the tool from inadvertently deploying. The tool is slidable relative to the catheter between a withdrawn position and an advanced position, with the tool being positioned proximal to the distal end of the catheter when in the withdrawn position and extending beyond the distal end of the catheter when in the advanced position. The retaining member is connected to the catheter proximal to the distal end of the catheter and is movable between a closed position and an open position. In the closed position, the retaining member prevents the tool from being prematurely deployed. In the open position, the retaining member allows the endoscopic tool to be deployed without interference. The retaining member is shaped in size to slidably fit within the interior area of the catheter so the axial walls of the catheter prevent the retaining member from moving toward the open position, thereby preventing the tool from moving toward the advanced deployed position until the catheter is moved distally to a selected position.

26 Claims, 4 Drawing Sheets

SAFE ENDOSCOPIC ACCESSORY

TECHNICAL FIELD

The present invention is directed toward endoscopic devices and more particularly toward endoscopic accessories used with endoscopes.

BACKGROUND OF THE INVENTION

The use of endoscopes for diagnostic and therapeutic indications is rapidly expanding. To improve performance, specialized endoscopes have been developed for specific uses. For example, there are upper endoscopes for examination of the esophagus, stomach and duodenum, colonoscopes for examining the colon, angioscopes for examining blood vessels, bronchoscopes for examining the bronchae, laparoscopes for examining the peritoneal cavity, and arthroscopes for examining joint spaces. The discussion which follows applies to all of these types of endoscopes and any modifications thereof.

There has been a large increase in the use of endoscopes for screening symptomatic and asymptomatic patients for gastrointestinal afflictions. These endoscopes are expensive and are used in contaminated and sensitive environments. Endoscopes typically have an insertion tube that is inserted into body cavities of a patient. The insertion tube of a conventional, non-sheathed endoscope includes a biopsy channel, suction channels, and air and water channels that extend along the length of the insertion tube. Endoscopic procedures are performed by passing the endoscopic accessory through a biopsy channel and out the distal end of the biopsy channel such that the distal end of the accessory extends into the body cavity and allows the physician to perform the endoscopic procedure. The insertion tube and associated biopsy channel follow the contours of a pathway through the patient's body cavity such that the biopsy channel must bend or curve several times along its length. Thus, the endoscopic accessory must be axially rigid yet flexible so it can be extended axially through the biopsy channels around the curves and bends in order to reach the distal end of the biopsy channel.

Improved endoscopes have been developed to be used with an endoscopic sheath, as is described in U.S. Pat. No. 4,646,722 to Silverstein et al. The endoscopic sheath includes an endoscope channel that receives and completely isolates the endoscope's insertion tube from the contaminated exterior environment. Biopsy, suction, air and water channels are positioned within the sheath substantially parallel to the endoscope channel. The biopsy, suction, air and water channel are all open at their distal ends to provide access to the patient's body cavity. When the endoscope and sheath assembly are used during an endoscopic procedure, the endoscopic accessory is moved through the biopsy channel until the distal end of the accessory is positioned adjacent to the distal end of the biopsy channel. Thereafter, the accessory can be extended into the patient's body cavity and deployed to perform part of the procedure and then retracted back into the distal end of the biopsy channel.

The endoscopic accessories typically have a tool at their distal end that is passed through the biopsy channel during the endoscopic procedure. When the tool is a rigid tool, such as a needle or forceps, the endoscope and sheath may be damaged if the tool prematurely deploys when the accessory is being passed through the biopsy channel. For example, a conventional endoscopic needle accessory typically includes an elongated catheter with a very sharp needle slidably disposed in the distal end of the catheter so the needle can be deployed by advancing it relative to the distal tip of the catheter. However, a conventional needle accessory does not prevent the needle from being inadvertently deployed when the accessory is being moved through the biopsy channel and when the distal end of the catheter is still within the biopsy channel.

If the tool is inadvertently and prematurely deployed, the tool the channel, or both can be damaged. The damaged equipment must then be repaired or replaced, and such repair or replacement is expensive, thereby greatly reducing the cost efficiency of endoscopic procedures. If the tool at the distal end of the accessory is a sensitive tool, such as a culture tube, a pH meter, a laser catheter, or the like, the tool can be contaminated or damaged if the tool is prematurely deployed. The contaminated or damaged equipment must be repaired or replaced, which substantially increases the cost and the time requirements of endoscopic procedures.

As a result of the above-described limitations in using an endoscope accessory by conventional techniques, the problem of premature deployment of endoscopic accessories with rigid or sensitive tools passing through biopsy channels has not been adequately solved.

SUMMARY OF THE INVENTION

The present invention is directed toward an endoscopic accessory which avoids the disadvantages of premature deployment experienced by other conventional accessories. In a preferred embodiment of the invention, the endoscopic accessory has a catheter with an endoscopic tool movably positioned within an interior area of the catheter. The endoscopic tool is movable between a retracted position within the interior area and an advanced position beyond the distal end of the catheter. A tool retaining member is attached to the distal end of the catheter and is movable between a closed position and an open position. In the closed position, the retaining member prevents the endoscopic tool from moving toward the advanced position, thereby retaining the endoscopic tool within the catheter and preventing premature deployment of the tool. In the open position, the retaining member is positioned away from the endoscopic tool and does not block the endoscopic tool, so as to allow the tool to move between the retracted and advanced positions.

In the closed position, the retaining member is shaped and sized to slidably fit within a biopsy channel of an endoscope or an endoscopic sheath, such that the biopsy channel prevents the retaining member from moving toward the open position before the retaining member has been moved beyond the distal end of the biopsy channel. After the retaining member has been moved beyond the distal end of the biopsy channel, the retaining member moves to the open position and the endoscopic tool is then deployed by moving it between the advanced and retracted positions.

In one embodiment of the invention, the retaining member is a two-piece protective cover movable between the closed and open positions, with the protective cover being in the closed position so as to surround and block the endoscopic tool from being deployed.

DETAILED DESCRIPTION OF THE INVENTION

Figure 1:
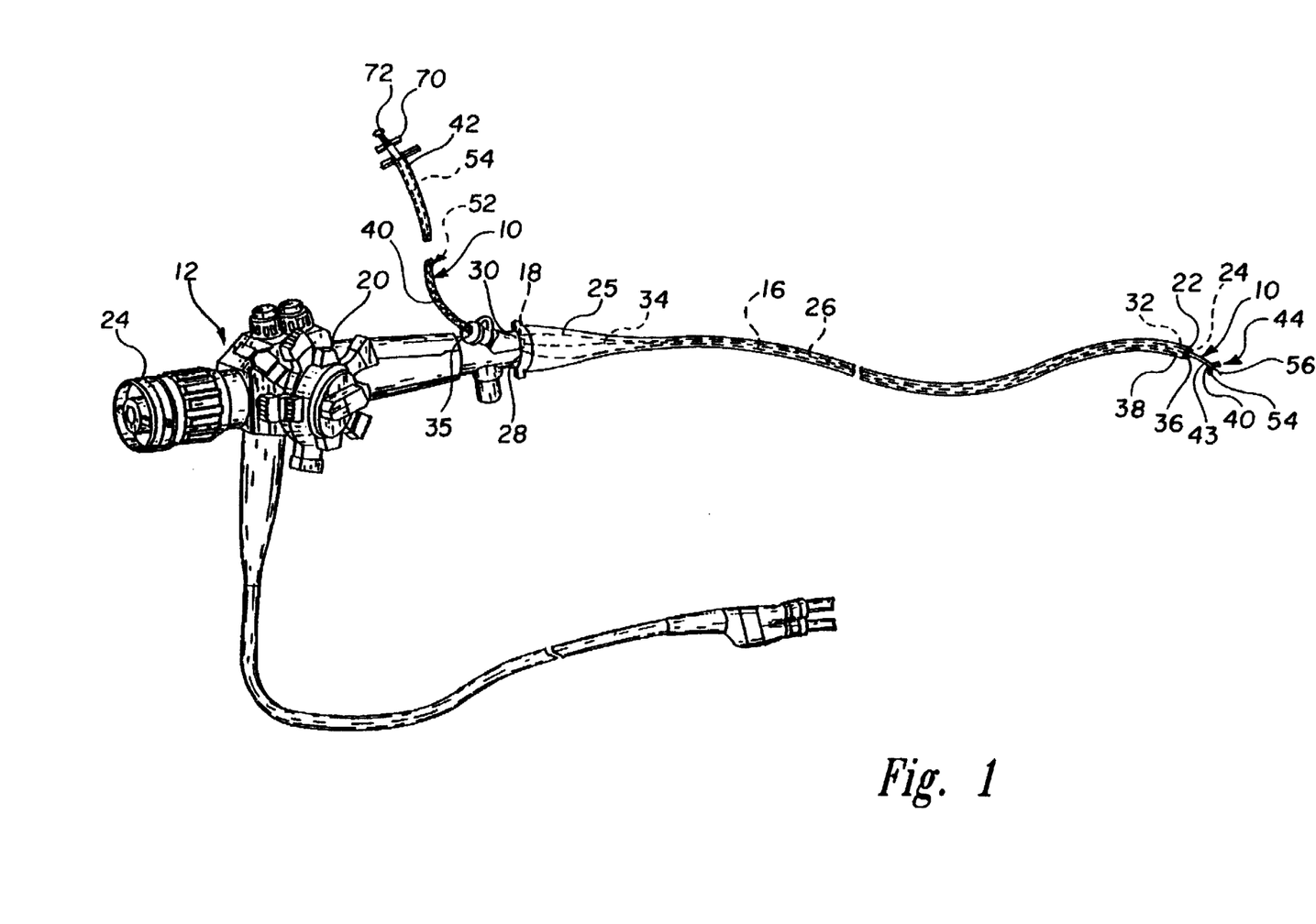
FIG. 1 is an isometric view of an endoscope and sheath assembly with an endoscopic accessory in accordance with the present invention positioned within a biopsy channel of the sheath.

As shown in FIG. 1, an endoscopic accessory 10 in accordance with the present invention extends through a sheathed endoscope 12 that is used by a physician to perform endoscopic procedures. The endoscope 12 has an elongated insertion tube 16 that connects at its proximal end 18 to a head piece 20. As is well known in the art, the insertion tube 16 includes a device for conveying an image from the insertion tube's distal end 22 to an eyepiece 24 connected to the headpiece 20 or to a TV monitor. A number of devices can be used to perform this function, including, for example, a lens that is optically coupled to the eyepiece 24 through an optical wave guide, or a miniature camera that is electronically coupled to a monitor. The imaging device enables the physician to see portions of the patient's body cavity and to see objects located just beyond the distal end 22 of the insertion tube 16 during the endoscopic procedure The insertion tube 16 is removably positioned within a sheath 25 to isolate the insertion tube from a contaminated environment during the endoscopic procedure. The sheath 25 has an endoscope channel 26 that receives the insertion tube 16 through an opening 28 at the sheath's proximal end 30. The distal end 32 of the endoscopic channel 26 is sealed to prevent the insertion tube 16 from being contaminated. The sheath 25 also has a biopsy channel 34 that is adjacent to the endoscope channel 26 along the length of the sheath. The biopsy channel 34 extends from an accessory receiving area 35 at the proximal end 30 of the sheath 25 and terminates at an opening 36 in the distal end 38 of the sheath. The biopsy channel 34 is shaped and sized to slidably receive the endoscopic accessory 10 therein. Although the preferred embodiment is described herein with reference to a sheathed endoscope 12 and the biopsy channel 34 within sheath 25, the endoscopic accessory 10 of the present invention can be used with other endoscopes, including a reusable endoscope having an insertion tube and a biopsy channel within the insertion tube. Therefore, the following description of the endoscopic accessory and its use with an endoscope is equally applicable to sheathed endoscopes, reusable endoscopes and other endoscopes and endoscopic devices.

The endoscopic accessory 10 has an elongated catheter 40 that has a length sufficient to extend through the entire length of the biopsy channel 34 with the proximal end 42 of the catheter located proximal to the accessory receiving area 35 and the distal end 43 of the catheter located distally beyond the distal end of the biopsy channel. An endoscopic tool 44 is operatively positioned at the distal end 43 of the catheter 40 and is used to perform an endoscopic procedure when the tool is deployed by extending it beyond the distal end of the biopsy channel 34, as discussed in greater detail below. The endoscopic accessory 10 is inserted into the distal end 43 of the catheter 40 into the accessory receiving area 35 and advanced axially through the biopsy channel 34 until the catheter's distal end is adjacent to the opening 36 in the distal end of the biopsy channel. From this position, the distal end of the catheter 40 and the tool 44 can be moved axially out of the biopsy channel 34.

Figure 2:
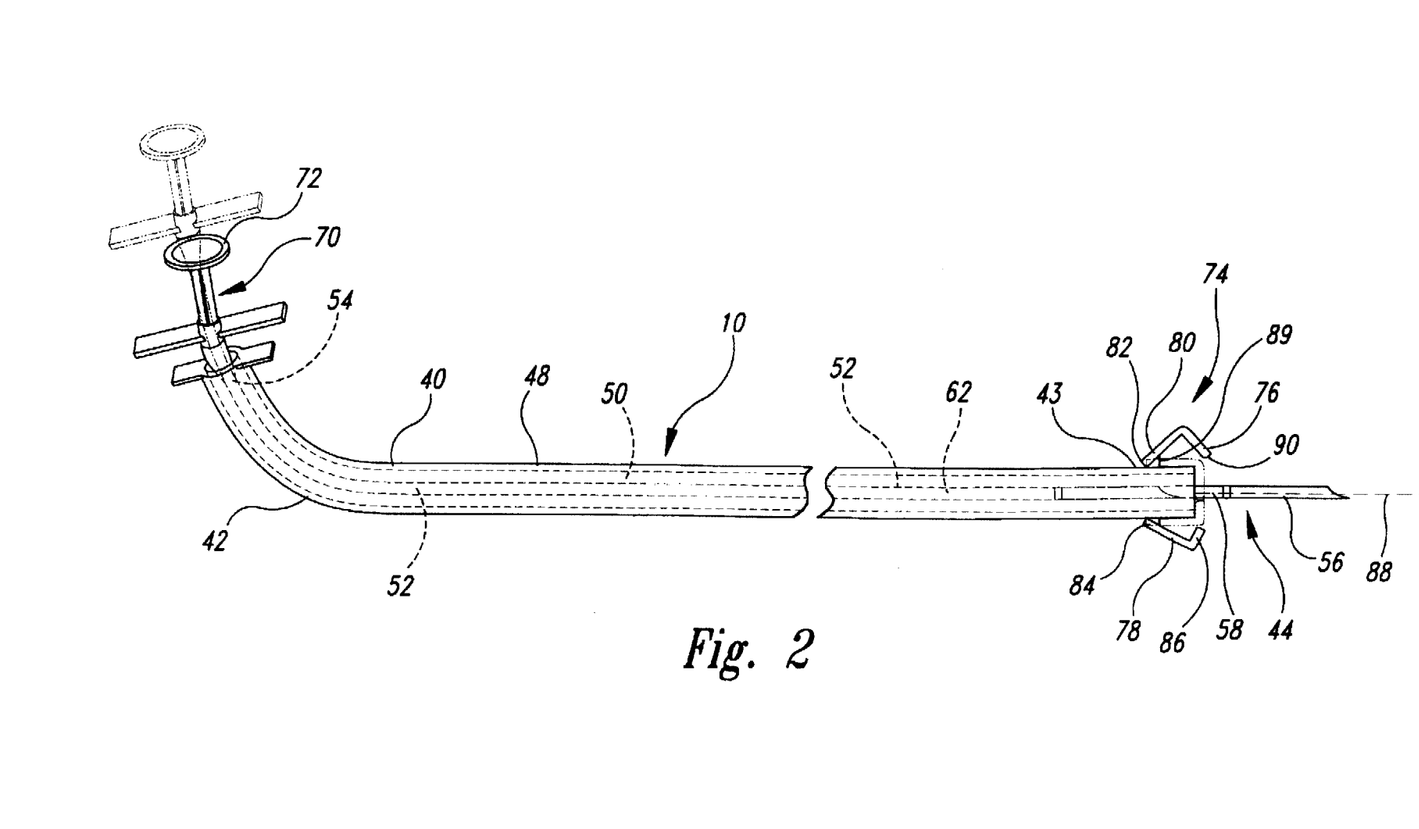
FIG. 2 is an enlarged partial side elevation view of the endoscopic accessory of FIG. 1 removed from the biopsy channel, and an endoscopic needle is shown in an advanced position and shown in phantom in a retracted position.

As best seen in FIG. 2, the catheter 40 of the endoscopic accessory 10 in accordance with the present invention has axial walls 48 that define an interior area 50 with a substantially circular cross-section. The interior area 50 is not limited to a circular cross section and other cross-sectional shapes could be used. The proximal and distal ends, 42 and 43, respectively, of the catheter 40 are open to provide access to the interior area 50. An elongated tool shaft 52 is slidably positioned within the interior area 50 of the catheter 40, and a proximal end 54 of the tool shaft is positioned proximal to the open proximal end of the catheter. The tool 44 of the illustrated embodiment is a hollow needle 56 that is connected in a conventional manner to the distal end 58 of the tool shaft 52, such that an interior channel 60 in the needle is axially aligned with an interior channel 62 of the tool shaft. The needle 56 is used to perform endoscopic procedures such as suctioning material from a lesion for diagnosis or for injecting material into tissue in the body cavity for treatment. Although the illustrated embodiment is shown and described using the needle, other endoscopic devices, such as biopsy forceps, a culture tube, a pH meter, an ultrasound device, a laser waveguide, etc., could be used with the catheter 40.

The needle 56 is movable relative to the distal end of the catheter 40 between a withdrawn, undeployed position, shown in phantom in FIG. 2, and an advanced, deployed position, shown in solid. In the withdrawn position, the needle 56 is contained within the catheter 40 so the sharp tip of the needle is just proximal to the catheter's open distal end 43 and is protected by the catheter. In the advanced position, the needle 56 is positioned distally beyond the distal end 43 of the catheter 40 and is no longer protected by the catheter. In this advanced position, the needle is in a ready position for performing the endoscopic procedure. Although the illustrated embodiment uses a hollow needle 56 on the distal end of the shaft 52, other sharp, rigid, and/or sensitive endoscopic tools can be used, including, as an example, forceps, a culture tube, a pH meter, a laser catheter, or the like.

The tool shaft 52 and needle 56 are shaped and sized to have a cross-sectional area that is slightly smaller than that of the inside cross-sectional area 50 of the catheter 40. Accordingly, the shaft 52 and needle 56 can be moved axially within the catheter, and radial movement of the shaft and needle within the catheter is minimized to maintain a high degree of control over the position of the needle by manipulating the proximal end 54 of the tool shaft 52.

The tool shaft 52 is a flexible member that bends and follows the contour of the catheter 40 and the biopsy channel 34 without restricting bending motion of the biopsy channel or the insertion tube. However, the tool shaft 52 is axially rigid so the shaft can be moved axially within the catheter 40 by pushing or pulling on the proximal end 54 of the shaft. Without such axial rigidity, pushing on the shaft would be like pushing axially on a string.

A control device 70 having a plunger 72 therein is connected to the proximal end 54 of the tool shaft 52 to control the needle 56. By axially pushing or pulling on the control device 70, the tool shaft 52 moves distally or proximally within the catheter 40, thereby moving the needle 56 between its undeployed and deployed positions. The plunger 72 is slidably positioned within the control device 70 to create suction forces so as to draw biopsy samples through the needle 56 and tool shaft 52, or to create positive pressure within the tool shaft and needle so as to inject medicament through the needle and into the patient for treatment. Although the illustrated embodiment uses a control device 70 with a plunger 72 therein, other control devices that control deployment of the needle 56 or other tool at the distal end of the tool shaft 52 can be used. These other control devices include hydraulic, automated, magnetic, etc., deployment methods.

As shown in FIG. 1, the proximal end 54 of the tool shaft 52, as well as the proximal end 42 of the catheter 40, are outside the proximal end of the biopsy channel 34 such that the control device 70 and plunger 72 are positioned near the headpiece 18 of the endoscope 12 and are easily accessible to the physician during the endoscopic procedure.

Figure 3:
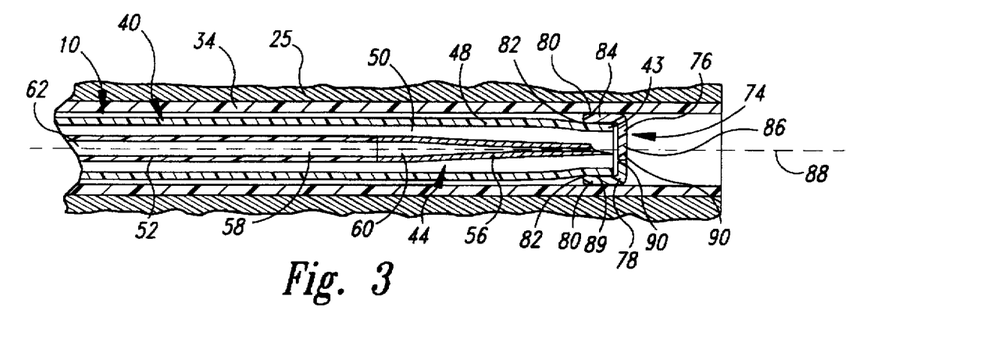
FIG. 3 is an enlarged cross-sectional view of the distal end of the endoscopic accessory of FIG. 2 positioned within the biopsy channel.
Figure 4:
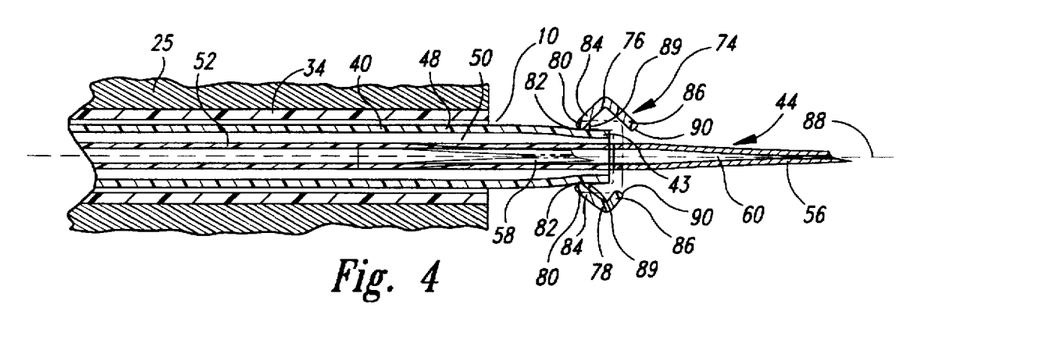
FIG. 4 is the cross-sectional view of FIG. 3 with the distal end of the endoscopic accessory extending distally from the biopsy channel, the endoscopic needle shown in solid extending from a catheter, and the endoscopic needle shown in phantom within the catheter.

As best seen in FIGS. 2, 3, and 4, the endoscopic accessory 10 has a retaining member 74 mounted to the catheter 40 adjacent to its open distal end 43. The retaining member 74 includes upper and lower protective covers 76 and 78 that are jaw-like attachments pivotally attached to the catheter's axial walls 48 on opposite sides of the catheter. Each of the upper and lower protective covers 76 and 78 have a rear end 80 attached to a hinge 82 that is secured to the axial wall 48 of the catheter 40. The upper and lower protective covers 76 and 78 pivot about the hinges 82 between a closed position, shown in FIG. 3, and an open position, shown in FIG. 4. In the open position, the upper and lower protective covers 76 and 78 do not block the open distal end 43 of the catheter 40 so the needle 56 can be moved distally to the advanced position and inserted into a target for diagnostic or therapeutic procedures. In the closed position, shown in FIG. 3, the upper and lower protective covers 76 and 78 completely block the open distal end 43 of the catheter 40 and the needle 56 is blocked from moving from the withdrawn position toward the advanced position. Although the retaining member 74 of the illustrated embodiment has two protective covers, 76 and 78, the retaining member can be constructed with one, three, four, five, or more protective covers that movably block the distal end of the catheter 40.

In one embodiment of the present invention, the retaining member 74 is permanently mounted to the catheter 40 at the time the accessory 10 is manufactured. In an alternate embodiment, the retaining member 74 is installed on a selected catheter 40, for example, to retrofit an existing catheter, or to prepare a desired catheter for performing an endoscopic procedure. The retaining member 74 of this alternate embodiment is either permanently affixed to the catheter 40, or is removably affixed. The removable retaining member 74 could be removed from the catheter after completion of the endoscopic procedure and disposed of, or alternatively, sterilized, disinfected, and reused.

Each of the upper and lower protective covers 76 and 78 have rear portions 84 that extend distally from the hinge 82 parallel to the catheter's axial walls 48 and connect to a forward portion 86 that bends inwardly toward the longitudinal axes of the catheter 40, shown schematically at 88. Each of the forward portions 86 terminates at a free end 90 opposite the rear end 80 of the protective covers, and the free ends are positioned immediately adjacent to each other when the upper and lower protective covers 76 and 78 are in the closed position. In the preferred embodiment the upper and lower protective covers 76 and 78 must open so that the distance between the free ends 90 is greater than or equal to the inside diameter of the catheter 40 in order for the needle 56 to move to the advanced position.

In the embodiment illustrated in FIGS. 3 and 4, the forward portion 86 of the upper protective cover 76 is slightly longer than the forward portion of the lower protective cover 78, so the free ends 90 of the upper and lower protective covers 76 and 78 meet at a position that is below the longitudinal axis 88 of the catheter. Accordingly, if the needle 56 is pushed toward the advanced position when the upper and lower protective covers 76 and 78 are in the closed position, as is the case when the catheter is in the withdrawn position, the sharp end of the needle will press against the upper protective cover 76 and be blocked from further distal motion. In an alternate embodiment not illustrated, the upper and lower protective covers 76 and 78 are the same size and their free ends 90 meet at the longitudinal axis 88 of the catheter 40. If the needle 56 is pushed toward the advanced position when the protective covers 76 and 78 are in the closed position, the sharp tip will wedge slightly into the area between the free ends but the needle will be blocked from prematurely moving to the advanced position. In another embodiment not illustrated, the free end 90 of the upper and lower protective covers 76 and 78 overlap each other when in the closed position.

The rear portions 84 of the upper and lower protective covers 76 and 78 are shaped and sized to partially extend around the distal end 43 of the catheter 40 and to slidably fit within the biopsy channel 34 when the upper and lower protective covers are in the closed position and the catheter is in the withdrawn position. Therefore, the upper and lower protective covers 76 and 78 do not deform the biopsy channel or create excessive frictional resistance to axial movement of the accessory 10 when the protective covers are in the closed position and the catheter is in the withdrawn position.

The hinge mechanisms 82 are connected to the catheter 40 proximal to the catheter's open distal end 43 so that the upper and lower protective covers 76 and 78 pivot about points that are proximal to the distal end of the catheter. In this arrangement, the rear portions 84 of the upper and lower protective covers 76 and 78 are positioned against or immediately adjacent to the axial walls of the biopsy channel when the protective covers are in the closed position and the catheter 40 is in the withdrawn position. As a result, the protective covers 76 and 78 are blocked by the biopsy channel 34 from pivoting about the hinge 82 and the upper and lower protective covers 76 and 78 can not move to the open position when the distal end 43 of the catheter 40 is within the biopsy channel. This prevents the needle 56 or other device from inadvertently or prematurely moving toward the advanced position.

When the distal end 43 of the catheter 40 is moved distally from the retracted position to the extended position, as best seen in FIG. 4, the upper and lower protective covers 76 and 78 are moved out of the biopsy channel 34 through the biopsy channel's open distal end. In this extended position, the upper and lower protective covers 76 and 78 are no longer blocked by the axial walls 48 of the biopsy channel 34 and the protective covers pivot about the hinge 82 from the closed position, shown in phantom, to the open position, shown in solid. In the open position, the upper and lower protective covers 76 and 78 are rotated away from the open distal end 43 of the catheter 40 to provide an unobstructed area that allows the needle 56 to move from the withdrawn position, shown in phantom, to the advanced position, shown in solid. When the upper and lower protective covers 76 and 78 are in the open position, the needle 56 is moved between the withdrawn and advanced positions when the shaft 52 is moved axially within the catheter by pushing or pulling on the control device 70, shown in FIG. 2.

A biasing spring 89 is connected to the hinge mechanisms 82 on each of the upper and lower protective covers 76 and 78 to urge the protective covers toward the open position. Thus, the protective covers 76 and 78 will pivot to the open position as soon as the distal end 43 of the catheter 40 is moved distally a sufficient distance beyond the end of the biopsy channel. The upper and lower protective covers 76 and 78 are shaped and sized such that they will not block the physician's view through the distal end of the insertion tube when the protective covers are in the open position. In one embodiment, the protective covers 76 and 78 spring back to a substantially flat position behind the distal end 43 of the catheter 40. In an alternate embodiment, not shown, the protective covers are removable and are constructed of a non-toxic material. The protective covers separate from the catheter after the catheter has been moved to the extended position. Thereafter, the needle or other tool is used to perform the therapeutic or diagnostic procedure, and the catheter is withdrawn proximally and removed from the biopsy channel. Once the removable covers have separated from the catheter, the needle or other device is only withdrawn after performing the selected endoscopic procedure, and the needle is not extended after being withdrawn.

As the catheter 40 is pulled proximally and moved from the extended position, shown in FIG. 4, toward the retracted position, shown in FIG. 3, the upper and lower protective covers 76 and 78 in the open position are pulled against the distal end of the biopsy channel 34. The biopsy channel 34, whether in the disposable sheath 25 or an insertion tube of a reusable endoscope, contacts on the upper and lower protective covers 76 and 78 just above the hinges 82 and the protective covers pivot from the open position to the closed position. Once the upper and lower protective covers 76 and 78 are pulled against the biopsy channel 34, and the protective covers are pivoted to the closed position, the catheter 40 moves to the retracted position. Thereafter, the catheter 40 and upper and lower protective covers 76 and 78 can be pulled completely within the biopsy channel 34 and withdrawn along the length of the biopsy channel.

The upper and lower protective covers 76 and 78 also provide a safety mechanism that interferes with withdrawal of the catheter through the biopsy channel 34 if the needle 56 has not completely moved from the advanced position to the withdrawn position. If the needle 56 has not been fully withdrawn when the catheter 40 is moved from the extended position toward the retracted position, the upper and lower protective covers 76 and 78 will partially close with the free ends 90 clamping onto the needle and the protective covers will not fully move to the closed position. The partially closed protective covers 76 and 78 will substantially resist the catheter 40 from being pulled proximally into the biopsy channel 34. In the preferred embodiment, the biopsy channel 34 is made of a flexible material that will deflect and stretch around the partially closed protective covers 76 and 78, but the physician will have to exert an increased proximal pulling force on the catheter 40 in order to draw the partially closed protective covers into the biopsy channel. Accordingly, a physician will notice an increased resistance upon moving the catheter 40 toward the retracted position when the needle 56 is in the advanced or partially advanced position, thereby indicating to the physician that such a condition exists.

In a conventional, reusable endoscope, the biopsy channel in the insertion tube is constructed of Teflon or the like which results in a substantially rigid channel in the radial direction. When the endoscopic accessory 10 is used with a reusable endoscope, the cross-sectional size of the biopsy channel is such that the catheter 40 could be withdrawn when the upper and lower covers 76 and 78 are partially closed or open, for example, if an urgent situation arises or if conditions require such retraction of the catheter. Such retraction will require an increase pulling force on the catheter 40. However, the cross-sectional size of the biopsy channel in the reusable endoscope is sufficiently small to block the upper and lower covers 76 and 78 from opening prematurely when the distal end 43 of the catheter 40 is within the biopsy channel.

The endoscopic accessory 10 of the present invention is used during an endoscopic procedure by inserting the distal end 43 of the catheter 40 into the biopsy channel 34, shown in FIG. 1, through the accessory receiving area 35. When the catheter 40 is inserted into the biopsy channel 34, the upper and lower protective covers 76 and 78 are in the closed position and the needle 56 is in the withdrawn position, as seen in FIG. 3. The distal end of the accessory 10 is moved through the biopsy channel to the retracted position with the distal end of the catheter 40 positioned just proximal to the distal end of the biopsy channel 34. Accordingly, the upper and lower protective covers 76 and 78 are held in the closed position as discussed above.

When the insertion tube 16 of the endoscope assembly 12 is positioned within a patient's body cavity at a desired location, the catheter 40 is moved distally in the biopsy channel 34 to the extended position with the distal end 43 of the catheter being positioned beyond the open distal end of the biopsy channel. Thereafter, the upper and lower protective covers 76 and 78 are moved from the closed position to the open position and the tool shaft 52 is moved distally through the interior area 50 of the catheter so as to move the needle 56 from the withdrawn position to the advanced position. With the needle 56 in the advanced position, the particular endoscopic procedure is performed, and the needle is then moved from the advanced position to the retracted position. Thereafter, the catheter 40 is retracted into the biopsy channel and the protective covers 76 and 78 are moved from the open position to the closed position, The endoscope assembly 12 can then be removed from the patient or, if another endoscopic accessory is to be used in the biopsy channel, the endoscopic accessory 10 is withdrawn from the biopsy channel through the accessory receiving area. The endoscopic accessory 10 is then discarded in a suitable receptacle for medical waste. Although the endoscopic accessory 10 of the preferred embodiment is inexpensive and disposable, the entire accessory of the present invention, or portions of the accessory, such as the shaft 52, the catheter 40, and the protective covers 76 and 78 can be cleaned, disinfected, and sterilized for subsequent use.

Figure 5:
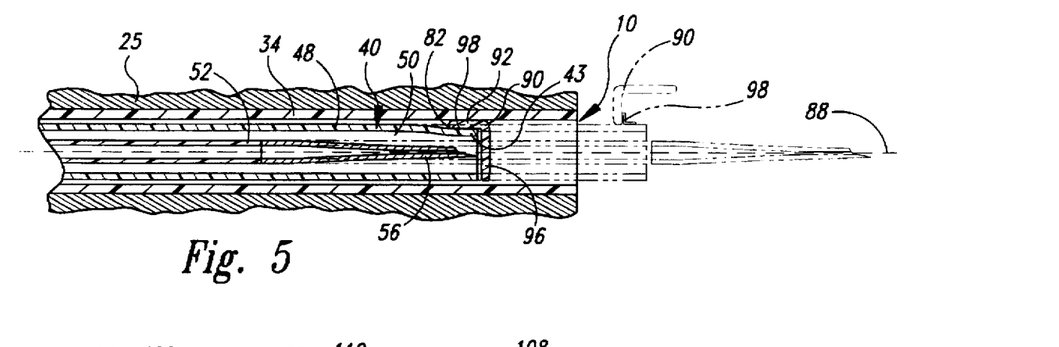
FIG. 5 is a partial cross-sectional view of the distal end of a first alternate embodiment of the present invention showing the catheter and endoscopic needle in solid within the biopsy channel and in phantom extending distally from the biopsy channel.

As best seen in FIG. 5, an alternate embodiment of the present invention has an L-shaped blocking member 90 with a first leg portion 92 that pivotally attaches to the axial wall 48 of the catheter 40 at the hinge 82. The hinge 82 is mounted to the catheter 40 proximal to the open distal end 43. A second leg portion 96 connects to the first leg portion 92 and is oriented at approximately 90° relative to the first leg portion. When the blocking member 90 is in a blocking position, shown in solid in FIG. 5, the first leg portion 92 extends distally from the hinge 82 parallel to the axial wall 48 of the catheter 40 and the second leg portion 96 bends downward transverse to the catheter's longitudinal axis 88 and extends across the catheter's open distal end 43. Thus, the second leg portion 96 provides a blocking surface that covers a majority of the opening and blocks the needle 56 from moving toward the advanced position while the distal end of the catheter is positioned within the biopsy channel 34.

When the catheter 40 is moved to the extended position, shown in phantom in FIG. 5, the blocking member 90 is pivoted from a closed position, shown in solid, to an open position that does not block the opening. A biasing mechanism 98 is connected to the first leg portion 92 adjacent to the hinge 82, and the biasing mechanism urges the blocking member 90 toward the open position. When the catheter 40 is moved proximally from the extended position toward the retracted position, the edge of the biopsy channel 34 engages the first leg portion 92 adjacent to the hinge 82 and causes the blocking member 90 to pivot from the open position to the closed position. The pivoting of the blocking member provides a similar safety mechanism as described above such that the blocking member 90 will not pivot to the fully closed position if the needle 56 is still fully or partially advanced.

Figure 6:
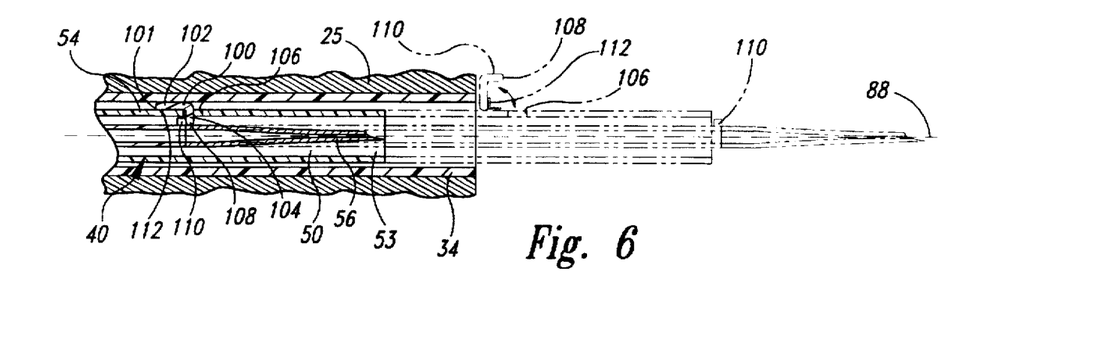
FIG. 6 is a partial cross-sectional view of the distal end of a second alternate embodiment of the present invention showing the catheter and endoscopic needle in solid within the biopsy channel and in phantom extending distally from the biopsy channel.

As best seen in FIG. 6, a second alternate embodiment of the endoscopic accessory 10 of the present invention is shown with an L-shaped lock 100 pivotally attached to the axial wall 48 of the catheter 40 at a position proximal to the catheter's distal end 43. The lock 100 is attached to the catheter 40 by a hinge 101, and a first leg 102 of the lock attaches at one end to the hinge and at the opposite end to a locking leg 104 that terminates at a free end 108. The locking leg 104 is oriented at approximately 90° relative to the first leg 102. The axial wall 54 of the catheter 46 has an aperture 106 formed therein between the catheter's distal end 53 and the hinge 101, and the aperture 106 is sized and positioned to receive at least a portion of the locking leg 104.

The lock 100 pivots about the hinge 101 between a lock position, shown in solid in FIG. 6, and a release position shown in phantom. The lock 100 is positioned and sized so the biopsy channel 34 blocks the lock from pivoting to the release position when the catheter is in the retracted position. In the lock position, the locking leg 104 extends through the aperture 106 and into the interior area 50 of the catheter 40. The needle 56 has a protrusion 110 extending axially therefrom and is sized and shaped such that the protrusion will be blocked from moving distally by the free end 108 of the locking leg 104. Thus, the locking leg 104 acts to block the protrusion 110 and the needle 56 from moving toward the advanced position from the withdrawn position.

When the catheter 40 is moved to the extended position, the lock 100 is urged to the release position by a biasing spring 112 connected to the first leg 102 adjacent to the hinge 101. In the release position, the lock 100 does not interfere with the axial movement of the needle 56. When the catheter 40 is moved proximally from the extended position toward the retracted position and the needle 56 is in the withdrawn position, the edge of the biopsy channel 34 engages the lock 100 and pivots the lock downwardly to the lock position so the locking leg 104 extends through the aperture 106 and locks the needle in the withdrawn position. Accordingly, the needle 56, or other device, must first be moved to the withdrawn position within the catheter 40 when the catheter is in the extended position. Thereafter, the catheter 40 is moved to the retracted position and the needle 56 is locked in the withdrawn position.

Figures 7, 8:
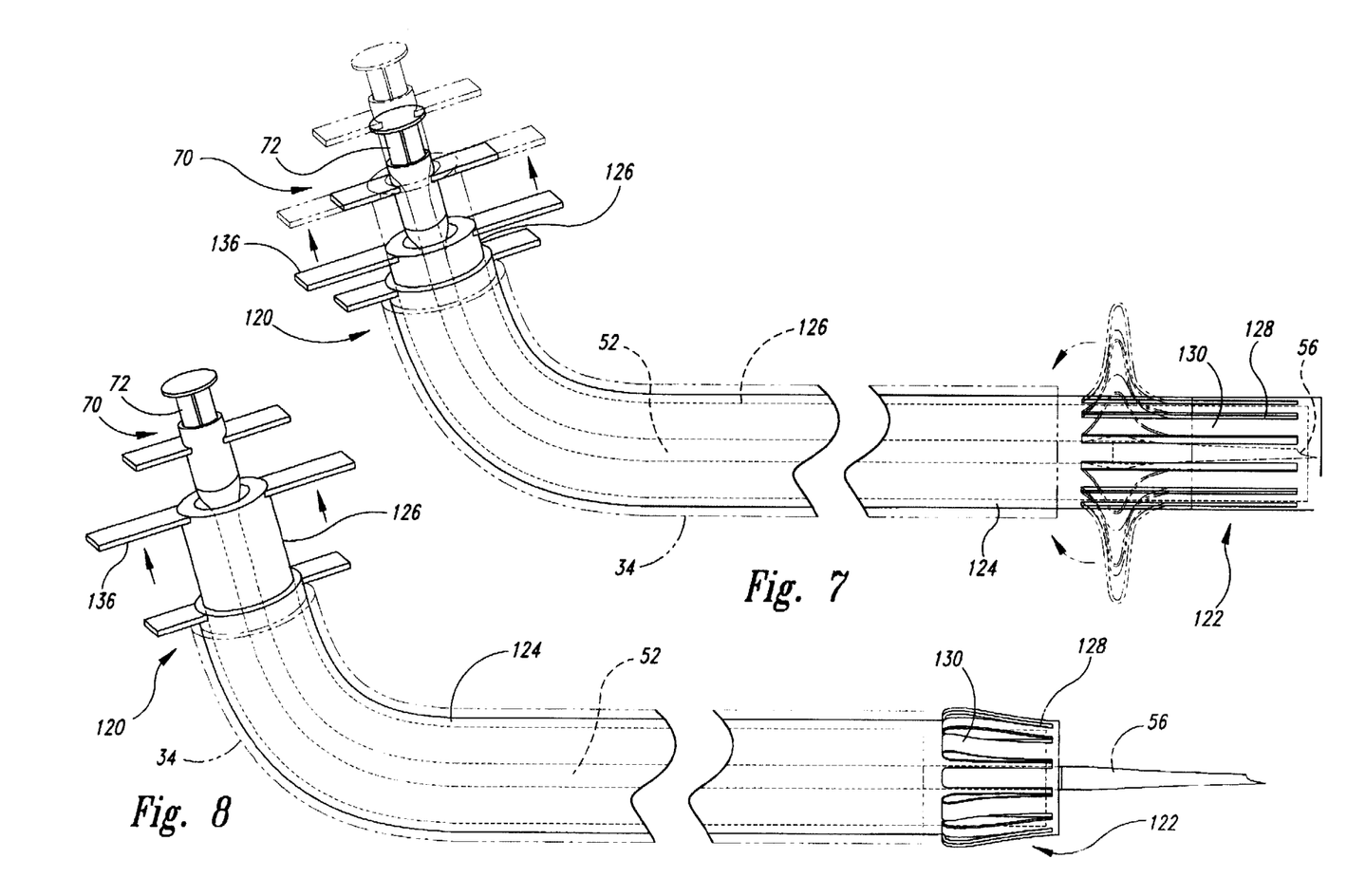
FIG. 7 is a partial side elevation view of a third alternate embodiment of the present invention showing the distal end of the catheter in phantom in an intermediate, flared position.
FIG. 8 is a partial side elevation view of the endoscopic accessory of FIG. 7 showing the distal end of the catheter in a folded position and the needle extending beyond the catheter's distal end.

As best seen in FIGS. 7 and 8, a third alternate embodiment of the present invention has a two-piece catheter 120 with a distal portion 122 that is movable from a closed position (FIG. 7) to a flared, retracted position (FIG. 8) only when the distal portion is not within the biopsy channel. The catheter 120 has an outer sleeve 124 and an axially rigid inner sleeve 126. The inner sleeve 126 is coaxially aligned and slidably positioned within the outer sleeve 124. The needle 56 and the tool shaft 52 are positioned within the inner sleeve 126 so the tip of the needle is proximal to the distal end of the catheter when the distal portion 122 is in the closed position. Thus, the needle 56 is completely contained within the catheter 120.

The outer sleeve 126 has a plurality of longitudinal slits 128 adjacent to its distal end, and the slits define a plurality of strips 130 around the distal portion 120. The slits 128 extend proximally along the outer sleeve 124 from just proximal to the catheter's distal end to an intermediate position along the length of the outer sleeve 124. The inner sleeve 126 is securely attached to the outer sleeve 124 only at the distal end of each sleeve, and the remaining portions of the inner sleeve are axially slidable relative to the outer sleeve and relative to the needle 56. The proximal end of the catheter 120 extends beyond the proximal end of the biopsy channel 34, and the proximal end of the inner sleeve 126 has a shoulder portion 136 that is adapted to be gripped by the physician and pushed or pulled axially. As the shoulder portion 136 is pulled, the inner sleeve 126 moves but the needle 56 and the majority of the exterior sleeve 124 remains stationary. The tool shaft 52 is securely coupled to the outer sleeve's proximal end, so the shaft and the needle 56 are restricted from moving relative to the outer sleeve's proximal end.

When the catheter 120 is in the closed position, as shown in solid in FIG. 7, the outer and inner sleeves 124 and 126 are coaxially arranged so the catheter is a cylindrical unit with substantially the same cross-sectional area along its entire length, and so the tip of the needle 56 is fully contained within the inner sleeve. In this closed position, the distal portion 122 of the catheter 120 slidably fits into the biopsy channel 34, which is shown in phantom in FIG. 7. The needle 56, or other device, remains protected within the catheter 120 until the catheter is moved to the extended position with the distal portion 122 beyond the distal end of the biopsy channel 34. The needle 56 is exposed when the physician pulls proximally on the inner sleeve's shoulder portion 136, thereby causing the distal end of the inner sleeve 126 to pull the distal end of the outer sleeve 124 proximally. As a result, the catheter's distal portion 122 moves from the closed position toward the flared, retracted position, and the strips 130 bow and flare radially outward away from the inner sleeve.

As the catheter's distal portion approaches the flared, retracted position, the strips 130 fold down around the outer sleeve 124, as illustrated in FIG. 8, and the needle 56 is exposed at the distal end of the catheter 120. The needle 56 is fully exposed when the catheter's distal portion is in the flared, retracted position. The strips 130 are shaped and sized so they will fold around the outer sleeve 124, but they will not interfere with the physician's view through the endoscope's imaging system. In an alternate embodiment, not shown, a folding mechanism, such as a fold line or the like, is provided on each of the strips at approximately the middle of the strip. The fold line allows the strips to pivot and fold about the fold line, thereby enabling the folded strips to set close to the catheter when the needle or other device is exposed.

The catheter 120 is constructed with its distal portion having a cross sectional area that is slightly smaller that the cross sectional area of the biopsy channel 34 when the distal portion 122 is in the closed position. The biopsy channel 34 blocks the strips 130 from bowing and flaring outwardly when the catheter's distal end is located within the biopsy channel. As a result, the outer and inner sleeves 124 and 126 cannot be retracted to expose the needle 56. Thus, the sharp needle 56 is completely contained in the catheter's distal portion 122 as the catheter 120 is moved through the biopsy channel 34. Only after the distal portion 122 is moved out of the biopsy channel 34 can the inner sleeve 126 be pulled proximally within the outer sleeve 124 and the needle 56 or other device be exposed to perform a therapeutic or diagnostic procedure.

The distal portion 122 is moved from the flared, retracted position to the closed position by pushing the inner sleeve 126 distally into the outer sleeve to contain the needle 56. The catheter's distal portion can also be moved to the closed position by pulling proximally on the outer sleeve 126 at its proximal end. The proximal movement of outer sleeve pulls the strips 130 against the distal end of the biopsy channel, and the strips 130 are pulled into the biopsy channel 34 as the distal portion is forced toward the closed position, thereby containing the needle 56. As discussed above, the biopsy channel 34 of the sheath is made of a flexible material, and the distal portion 122 of the catheter 120 could be withdrawn into the biopsy channel when the distal portion is in the flared, retracted position if necessary, although the physician will have to exert an increased proximal pulling force on the catheter because of the increased resistance to withdrawal of the catheter. Similarly, the catheter 120 can be withdrawn into the biopsy channel of a reusable endoscope if necessary when the distal portion is in the flared, retracted position by exerting an increased proximal pulling force on the catheter.

Numerous modifications and variations of the safe endoscopic accessory invention disclosed herein will occur to those skilled in the art in view of this disclosure. Other shapes and sizes of blocking mechanisms can be connected to the distal end of the catheter to block movement of a selected endoscopic tool from moving toward the advanced position when the catheter is in the retracted position within the biopsy channel. For example, the catheter can have three, four, five or more blocking members positioned around the catheter's distal end that are adapted to move between the open and blocking positions. Also, although the inventive safe endoscopic accessory has been described as being inserted through the biopsy channel of a protective sheath for an endoscope, it will be understood that it may also be inserted through the biopsy channel of an endoscope which is reusable and contains a biopsy channel. Therefore, it is to be understood that these modifications and variations, and equivalents thereof, may be practiced while remaining within the spirit and the scope of the invention as defined in the following claims.

What is claimed is:

1. An endoscopic accessory and tubular member combination, comprising:

a tubular member having first axial walls defining a channel;

a catheter movably positioned in said channel, said catheter having an open distal end and second axial walls defining an interior area;

an endoscopic tool positioned within said interior area, said endoscopic tool being movable relative to the catheter between a protected position with a first end of said endoscopic tool within said interior area and an exposed position with said first end of said endoscopic tool exposed through said open distal end; and a retaining member connected to said catheter adjacent to said open distal end, said retaining member selectively retaining said endoscopic tool in said protected position, said retaining member being movable between a first position with said endoscopic tool being prevented from moving toward said exposed position and a second position with said retaining member being positioned to allow said endoscopic tool to move relative to said catheter toward said exposed position, said retaining member being sized to fit within said channel when said endoscopic tool is in said protected position, said first axial walls of said tubular member blocking said retaining member from moving to said second position.

2. The endoscopic accessory and tubular member combination of claim 1 wherein said endoscopic tool includes a shaft and a therapeutic or diagnostic tool attached to the distal end of said shaft.

3. The endoscopic accessory and tubular member combination of claim 2 wherein said therapeutic or diagnostic tool is a needle.

4. The endoscopic accessory and tubular member combination of claim 1 wherein said retaining member is a blocking device that is movably positioned adjacent to said distal end of said catheter and that blocks said endoscopic tool from extending through said open distal end of said catheter when said retaining member is in said first position.

5. The endoscopic accessory and tubular member combination of claim 1 wherein said retaining member includes a cover pivotally attached to said catheter adjacent to said distal end, said cover being arranged in said first position to close said open distal end of said catheter, and said cover being open and positioned away from said open distal end when said cover is in said second position to allow said endoscopic tool to be moved relative to the catheter toward said exposed position.

6. The endoscopic accessory and tubular member combination of claim 1 wherein said retaining member includes first and second covers pivotally attached to said catheter adjacent to said distal end, said first and second covers being arranged in said first position to engage each other and to close said open distal end of said catheter, and said first and second covers being open and spaced apart from each other when said first and second covers are in said second position to allow said endoscopic tool to be moved relative to the catheter toward said exposed position.

7. The endoscopic accessory of claim 1 wherein said catheter includes an inner sleeve and an outer sleeve connected to said inner sleeve, said endoscopic tool is coupled to said outer sleeve to restrict said endoscopic tool from moving relative to said outer sleeve, said inner sleeve is movable relative to said outer sleeve and relative to said endoscopic tool, said retaining member includes a plurality of flexible members connected to said outer sleeve and coupled to said inner sleeve, said flexible members being movable between said first position and second position, with said flexible members being immediately adjacent to said inner sleeve when in said first position and said flexible members being flared radially outward away from said inner sleeve when in said second position, and said endoscopic tool is held in said withdrawn position when said flexible members are in said first position, and said endoscopic tool being movable toward said advanced position only when said flexible members move from said first position toward said second position.

8. The endoscopic accessory and tubular member combination of claim 1 wherein said catheter has a second end opposite said first end, and said endoscopic accessory further comprising a control device having proximal and distal ends, said control device being coupled at said proximal end to said second end of said catheter, and said control device being connected to said endoscopic tool to control the movement of said endoscopic tool relative to said catheter.

9. An endoscopic accessory and tubular member combination, comprising:
- a tubular member having axial walls defining a channel;
- a catheter movably positioned in said channel, said catheter having proximal and distal ends and second axial walls defining an interior area;
- a tool assembly having an elongated member positioned within said interior area of said catheter, said elongated member having proximal and distal ends, and said tool assembly having an endoscopic tool attached to said distal end of said elongated member, said tool assembly being axially movable relative to said interior chamber to move said endoscopic tool between a protected position and an exposed position, said endoscopic tool being positioned within said interior area of said catheter when said endoscopic tool is in said protected position, and said endoscopic tool being exposed at said distal end of said catheter when said endoscopic tool is in said exposed position; and
- a retaining member connected to said catheter adjacent to said distal end, said retaining member being movable between first and second positions, said retaining member being positioned to prevent said endoscopic tool from moving out of said catheter toward said exposed position when said retaining member is in said first position, and said retaining member being positioned to allow said endoscopic tool to move out of said catheter toward exposed said position when said retaining member is in said second position, said retaining member being sized to fit within said channel when said endoscopic tool is in said protected position, said first axial walls of said tubular member blocking the retaining member from moving toward said second position.

10. The endoscopic accessory and tubular member combination of claim 9 wherein said endoscopic tool is a needle.

11. The endoscopic accessory and tubular member combination of claim 9 wherein said retaining member is a blocking member that is movably positioned adjacent to said distal end of said catheter and that covers said distal end of said catheter when said retaining member is in said first position to block said endoscopic tool from moving relative to the catheter toward said exposed position.

12. The endoscopic accessory and tubular member combination of claim 9, further comprising a biasing member connected to said retaining member, said biasing member urging said retaining member toward said second position.

13. The endoscopic accessory and tubular member combination of claim 9 wherein said endoscopic tool is proximal to said distal end of said catheter and completely contained within said interior area of said catheter when said endoscopic tool is in said protected position.

14. The endoscopic accessory and tubular member combination of claim 9 wherein said retaining member includes first and second members pivotally attached to said catheter adjacent to said distal end, said first and second members being arranged in said first position to close said distal end of said catheter, and said first and second members being open and spaced apart from each other when said first and second members are in said second position to allow said endoscopic tool to move through said distal end toward said exposed position.

15. The endoscopic accessory and tubular member combination of claim 9 wherein said catheter has a second end opposite said first end, and said tool assembly includes a tool control device connected to said proximal end of said elongated member, said tool control device being coupled to said endoscopic tool to control the movement of said endoscopic tool relative to said catheter.

16. An endoscopic accessory and tubular member combination comprising:
- a tubular member having first axial walls defining a channel;
- a catheter movably positioned in the tubular member, the catheter having a distal end;
- an endoscopic tool being at least partially movable relative to said distal end of said catheter; and
- a retaining member connected to said catheter adjacent to said distal end, said retaining member being movable between open and closed positions, said endoscopic tool being deployed for performing a therapeutic or diagnostic endoscopic procedure when said retaining member is in said open position, and said endoscopic tool being undeployed and blocked from performing a therapeutic or diagnostic endoscopic procedure when said retaining member is in said closed position said member is sized to fit within said channel when said endoscopic tool is undeloyed, said axial walls of said tubular member blocking said retaining member from moving toward said open position when said endoscopic tool is in said undeployed position.

17. The endoscopic accessory and tubular member combination of claim 16 wherein said retaining member includes first and second covers pivotally attached to said catheter adjacent to said distal end.

18. The endoscopic accessory and tubular member combination of claim 17 wherein said first and second covers are positioned to engage each other when in said closed position, and said first and second covers being spaced apart from each other when in said open position with said endoscopic tool being deployed.

19. An endoscope and endoscopic accessory assembly, comprising:
- an endoscope having first axial walls forming a channel with proximal and distal ends, said channel having an opening at said distal end; and
- an endoscopic accessory movably positioned in said channel, said endoscopic accessory comprising:
- a catheter with proximal and distal ends and second axial walls defining an interior area of said catheter, said catheter being movable relative to said channel between a retracted position and an extended position, said catheter in said retracted position having said distal end of said catheter positioned within said channel proximal to said opening in said distal end of said channel, and said catheter in said extended position having said distal end of said catheter extending through said opening at said distal end of said channel;

an endoscopic tool positioned within said interior area of said catheter, said endoscopic tool having a distal end and being movable between a protected position and an exposed position, said distal end of said endoscopic tool being positioned within said interior area of said catheter proximal to said distal end of said catheter when said endoscopic tool is in said protected position, and said distal end of said endoscopic tool being positioned exterior of said interior area and distal from said distal end of said catheter when said endoscopic tool is in said position; and a retaining member connected to said catheter adjacent to said distal end, said retaining member being movable between first and second positions, said retaining member in said first position being positioned to prevent said endoscopic tool from moving toward said exposed position, and said retaining member in said second position being positioned to allow said endoscopic tool to move from said protected position toward said exposed position, said retaining member being sized to fit within said channel when said endoscopic tool is in said protected position, said retaining member movable to engage said first axial walls of said channel when said endoscopic tool is in said protected position with said first axial walls blocking said retaining member from moving to said second position.

20. The endoscope and endoscopic accessory assembly of claim 19 wherein said endoscope includes an elongated insertion tube having proximal and distal ends and an endoscopic sheath having a second channel that removably receives said elongated insertion tube within said second channel to shield said insertion tube from an external environment, and said sheath further includes said first channel with said first channel being isolated from said elongated insertion tube, and said endoscopic accessory positioned within said first channel being isolated from said elongated insertion tube.

21. The endoscope and endoscopic accessory assembly of claim 19 wherein said endoscopic tool includes a shaft and a therapeutic or diagnostic tool attached to a distal end of the shaft.

22. A medical device for inserting into a selected body cavity of a patient during a therapeutic or diagnostic medical procedure, comprising:

an outer tubular member having a first distal end and first axial walls defining a channel, the outer tubular member being adapted to extend into the selected body cavity with the first distal end being in the selected body cavity;

an inner tubular member movably positioned in the channel of the outer tubular member, the inner tubular member having a second distal end and second axial walls defining an interior area;

a diagnostic or therapeutic tool assembly positioned within the interior area for relative movement between the tool assembly and the inner tubular member, the tool assembly being positionable in a protected position with a first end of the tool assembly within the interior area of the inner tubular member and an exposed position with the first end of the tool assembly being exposed at the second distal end; and a retaining member connected to the inner tubular member adjacent to the second distal end, the retaining member selectively preventing the relative movement between the tool assembly and the inner tubular member to retain the tool assembly in the protected position, the retaining member being movable between a first position with the tool assembly being in the protected position and prevented from being positioned to the exposed position and a second position with the retaining member being positioned to allow the tool assembly to be positioned in the exposed position, the retaining member being sized to fit within the channel when the tool assembly is in the protected position, the first axial walls blocking the retaining member from moving radially outwardly relative to the inner tubular member to the second position.

23. The device of claim 22 wherein the diagnostic or therapeutic tool assembly includes a needle.

24. The device of claim 22 wherein the retaining member is a blocking device that is movably positioned adjacent to the second distal end of the inner tubular member and that blocks the tool assembly from extending through the second distal end of the inner tubular member when the retaining member is in the first position.

25. The device of claim 22 wherein the inner tubular member is a catheter, and the retaining member includes a cover pivotally attached to the catheter adjacent to the second distal end, the cover being arranged in the first position to close the second distal end of the catheter, and the cover being open and positioned away from the second distal end when the cover is in the second position to allow the tool assembly to be positioned in the exposed position.

26. The device of claim 22 wherein the outer tubular member is an insertion tube of an endoscope.

* * * * *

UNITED STATES PATENT AND TRADEMARK OFFICE
CERTIFICATE OF CORRECTION

PATENT NO. : 5,702,344
DATED : December 30, 1997
INVENTOR(S) : Fred E. Silverstein It is certified that error appears in the above-identified patent and that said Letters Patent is hereby corrected as shown below:

In column 13, claim 9, line 50, following "toward", please delete "exposed said" and insert therefor --said exposed--.

In column 15, claim 19, line 16, following "said", please insert therefor --exposed--.

Signed and Sealed this

Twentieth Day of October, 1998

Attest:

BRUCE LEHMAN

*Attesting Officer*   *Commissioner of Patents and Trademarks*